United States Patent [19]
Kinkel et al.

[11] Patent Number: 5,879,953
[45] Date of Patent: Mar. 9, 1999

[54] SPECIAL CHEMILUMINESCENT ACRIDINE DERIVATIVES AND THE USE THEREOF IN LUMINESCENCE IMMUNOASSAYS

[75] Inventors: Tonio Kinkel, Frankfurt am Main; Peter Molz, Mainz; Erwin Schmidt, Kelkheim; Gerd Schnorr, Bad Vilbel; Heinz Jürgen Skrzipczyk, Bad Soden am Taunus, all of Germany

[73] Assignee: Hoechst Aktiengesellschaft, Frankfurt am Main, Germany

[21] Appl. No.: 479,196

[22] Filed: Jun. 7, 1995

Related U.S. Application Data

[62] Division of Ser. No. 93,694, Jul. 20, 1993, which is a continuation of Ser. No. 311,912, Feb. 17, 1989, abandoned.

[30] Foreign Application Priority Data

Feb. 20, 1988 [DE] Germany .......................... 38 05 318.7

[51] Int. Cl.$^6$ ...................... G01N 33/533; G01N 33/543
[52] U.S. Cl. ...................... 436/518; 436/500; 436/546; 436/800; 530/391.3
[58] Field of Search ................... 436/800, 518, 436/546, 500; 530/391.3

[56] References Cited

U.S. PATENT DOCUMENTS

| | | |
|---|---|---|
| 3,352,791 | 11/1967 | Sheehan et al. . |
| 4,745,181 | 5/1988 | Law et al. ............................... 546/104 |
| 4,946,958 | 8/1990 | Campbell et al. . |
| 5,468,646 | 11/1995 | Mattingly et al. ....................... 546/104 |

FOREIGN PATENT DOCUMENTS

| | | |
|---|---|---|
| 1316363 | 5/1973 | European Pat. Off. . |
| 1548741 | 7/1979 | European Pat. Off. . |
| 82636 | 6/1983 | European Pat. Off. . |
| 135071 | 3/1985 | European Pat. Off. . |
| 170415 | 2/1986 | European Pat. Off. . |
| 0 216 553 | 4/1987 | European Pat. Off. . |
| 0 257 541 | 3/1988 | European Pat. Off. . |
| 0 273 115 | 7/1988 | European Pat. Off. . |
| 2618511 | 4/1976 | Germany . |
| 2618419 | 11/1976 | Germany . |
| 3628573 | 2/1988 | Germany . |
| 1461877 | 1/1977 | United Kingdom . |
| 2008247 | 5/1979 | United Kingdom . |
| 2041920 | 9/1980 | United Kingdom . |

OTHER PUBLICATIONS

W.P. Collins, Alternative Immunoassays, John Wiley & Sons Ltd., Chichester (1985), (Table of Contents).
J.A. Matthews, et al., Analytical Biochemistry 151, 205–209 (1985).
H.R. Schroeder et al., Methods in Enzymology, vol. LVII, 424–445, Academic Press Inc., New York (1978).
W.G. Wood, J. Clin. Chem. Clin. Biochem., vol. 22, 905–918 (1984).
F. McCapra, Acc. Chem Res., vol. 9, 201–208 (1976).
F. McCapra, Progress in Organic Chem., vol. 8, 231–277 (1973).
Lehmstedt & Hundertmark, vol. 63, 1229–1241 (1930).
Lehmstedt & Wirth, vol. 61, 2044–2049 (1928).
I. Weeks et al., "Acridinium Esters as High–Specific–Activity Labels in Immunoassay," Clin. Chem. vol. 29, No. 8, Aug. 1983, 1474–1479.

*Primary Examiner*—Mary E. Ceperley
*Attorney, Agent, or Firm*—Finnegan, Henderson, Farabow, Garrett & Dunner, L.L.P.

[57] ABSTRACT

Chemiluminescent acridinium derivatives of the formula I

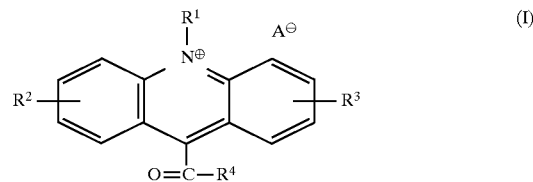

in which $R^4$ represents a radical of the formula II or III

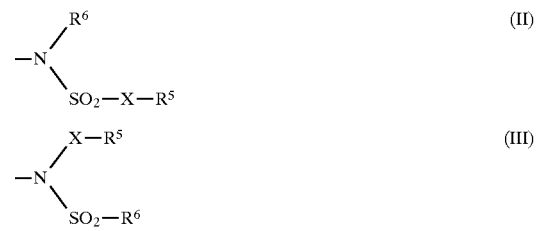

and $A^\ominus$, X—, $R^1$–$R^3$, $R^5$ and $R^6$ have the stated meanings, as well as processes for the preparation of the compounds of the formula (I) and the use thereof in chemiluminescence immunoassays.

15 Claims, 3 Drawing Sheets

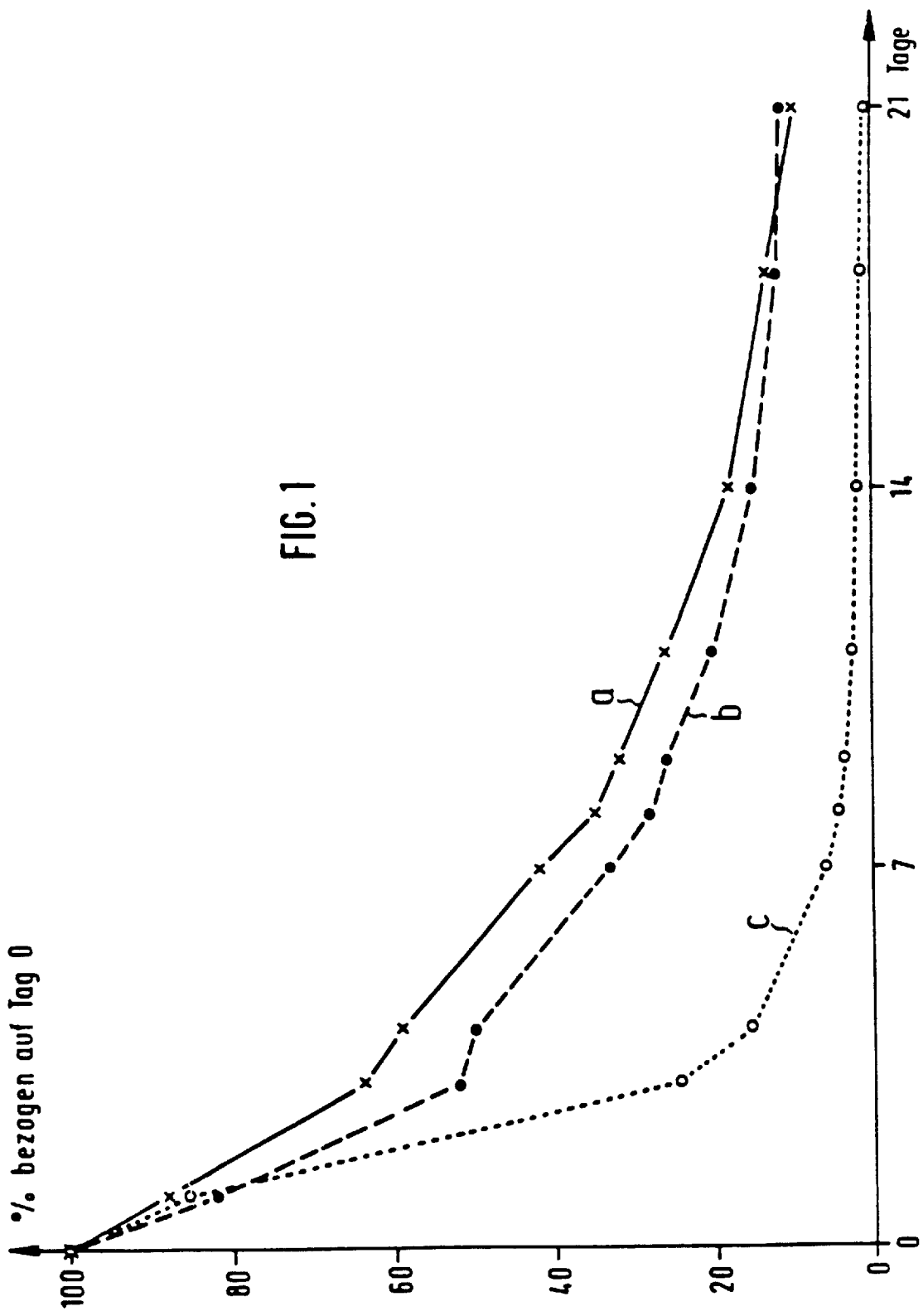

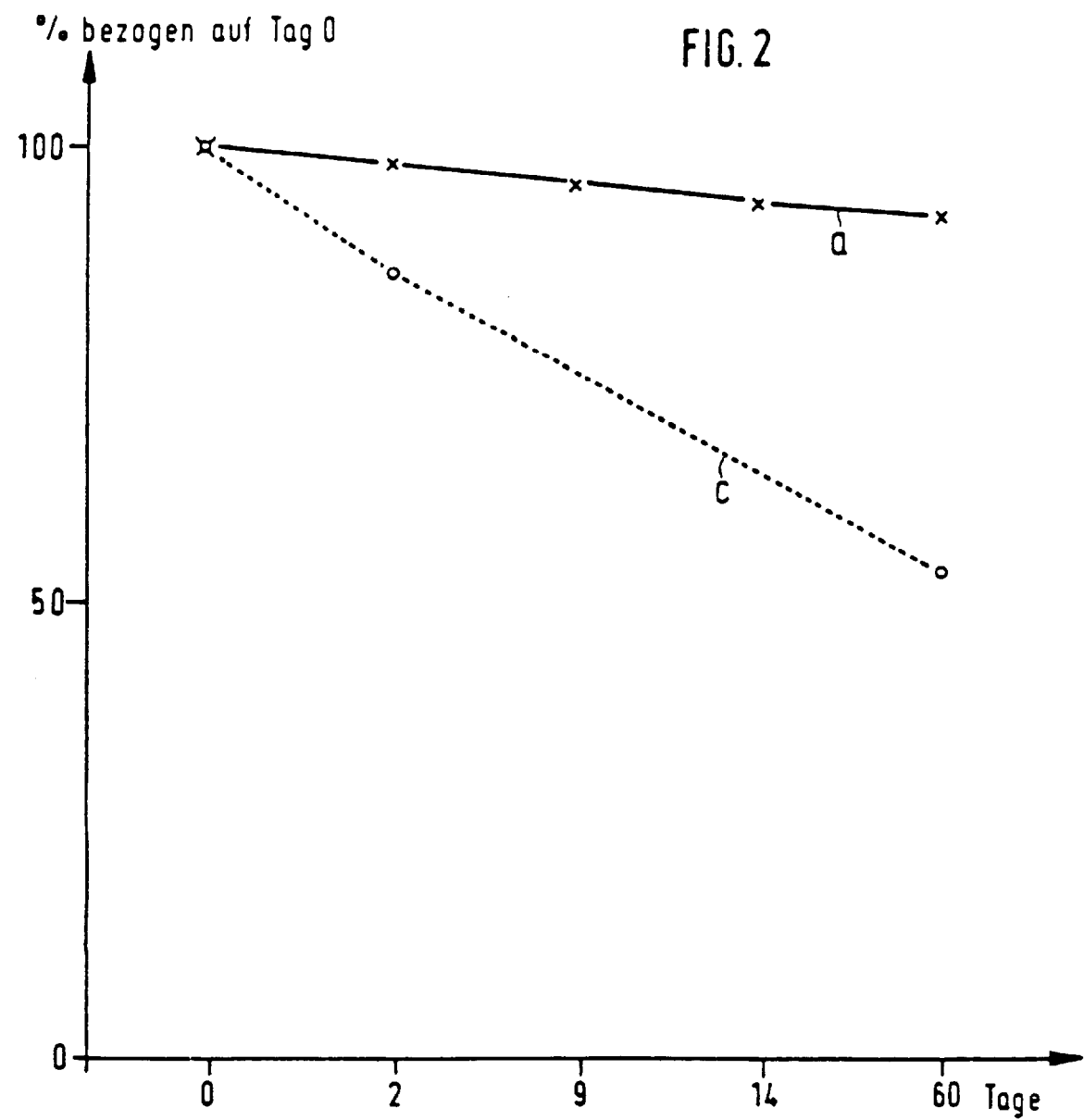

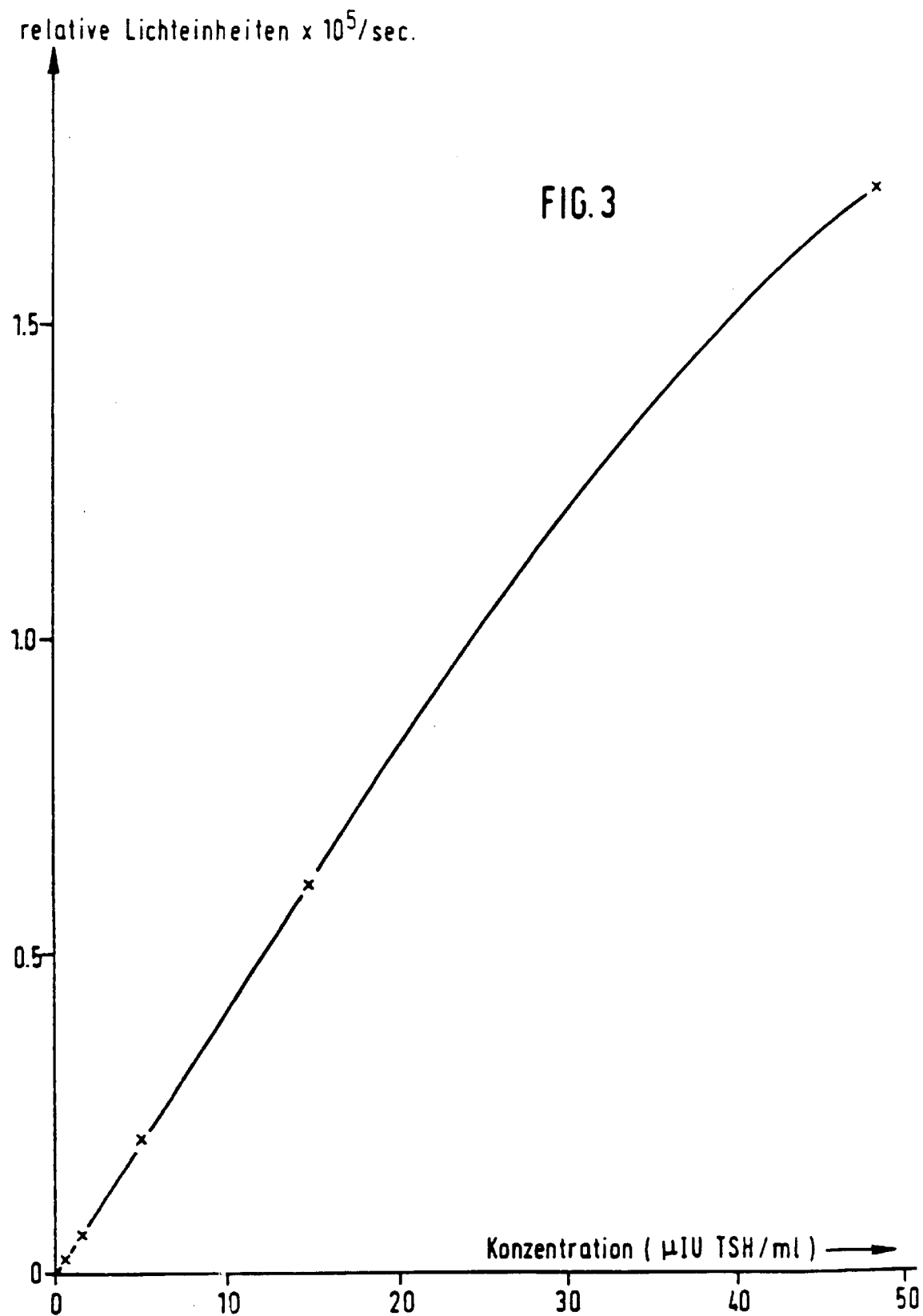

SPECIAL CHEMILUMINESCENT ACRIDINE DERIVATIVES AND THE USE THEREOF IN LUMINESCENCE IMMUNOASSAYS

This is a division of application Ser. No. 08/093,694, filed Jul. 20, 1993, which in turn is a continuation of prior application Ser. No. 07/311,912, filed Feb. 17, 1989, now abandoned, which applications are herein incorporated by reference, in their entirety.

The present invention relates to chemiluminescent acridine derivatives, to processes for the preparation thereof and to the use thereof in luminescence immunoassays.

Luminescent compounds already have a wide variety of uses. They are employed as indicators in bioassays, enzyme immunoassays and luminescence immunoassays (cf. W. P. Collins "Alternative Immunoassays", published by John Wiley & Sons Ltd., Chichester, 1985) but are also used in nucleic acid hybridization assays (cf. J. A. Matthews et al. "Analytical Biochemistry", 151, 205–209, 1985). In addition, chemiluminescent compounds are employed in flow injection analysis, in post-column detectors in liquid chromatography, in flow research and in artificial light sources.

Chemiluminescent marker substances of two structural types in particular have acquired relatively great significance in chemiluminescence immunoassays. These are, on the one hand, the derivatives of luminol and isoluminol, which are described by H. R. Schroeder et al., "Methods in Enzymology", Academic Press Inc., New York, Vol. LVII, 1978, 424 et seq., and in British Patents 2,008,247 and 2,041,920, German Patents 26 18 419 and 26 18 511, as well as European Patent Application 135,071. A review of the use in practice of the isoluminol compounds as luminescence indicators is to be found in W. G. Wood, J. Clin.Chem. Clin. Biochem. 22, 1984 905–918.

On the other hand, acridinium ester compounds have also been used as chemiluminescence marker substances. Such acridinium esters are disclosed in U.S. Pat. No. 3,352,791, British Patents 1,316,363 and 1,461,877 and European Patent Application 82,636. The use of acridinium esters as marker substances in immunoassays is described by Weeks et al., Clin. Chem. 29/8 (1983), 1474–1479. The use of phenanthridinium esters as marker substances in luminescence immunoassays has also been disclosed, in European Patent Application 170,415.

The chemiluminescence of acridinium esters can be initiated by addition of alkaline $H_2O_2$ solution. A convincing explanation of the mechanism of the chemiluminescence has been given by F. McCapra, Acc.Chem. Res. 9, 201, 1976. It is apparent from this that the nature of the leaving group is crucial both for the quantum yield of light and for the hydrolytic stability.

The acridinium esters which have hitherto been disclosed have the advantage over the luminol and isoluminol compounds that the quantum yield of light is higher and is not adversely affected by proteins bound to the indicator (cf. Weeks et al., Clin. Chem. 29/8 (1983), 1474–1479).

Although the acridinium phenyl esters disclosed in European Patent Application 82,636 are distinguished by a high detection sensitivity when the chemiluminescence is excited by mild oxidizing agents, they have disadvantages which interfere with practical use. In particular, the phenyl ester linkage is very labile in aqueous systems, even at room temperature. An additional factor is that, under the oxidation conditions stated therein, the acridinium phenyl esters show an emission of light which has substantially, i.e. above 95%, disappeared only after about 10 seconds. By comparison with this, other non-isotopic assay methods have far shorter measurement times and thus allow a higher sample throughput.

It has already been proposed to use chemiluminescent acridinium derivatives which, together with a high quantum yield of light, have more rapid reaction kinetics and thus allow short measurement times for a luminescence immunoassay (cf. German Patent Application P 36 28 573.0). These take the form of acridinium derivatives of the formula

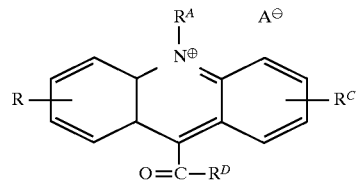

in which $R^A$ is hydrogen, an alkyl, alkenyl or alkynyl radical having 1 to 10 carbon atoms, or a benzyl or aryl group, $R^B$ and $R^C$ are hydrogen, an alkyl group having 1 to 4 carbon atoms, a substituted or unsubstituted amino group, a carboxyl, alkoxy, cyano or nitro group or halogen, $R^D$ represents a radical in which a sulfonamide group is directly bonded via the nitrogen to the carbonyl group, or is a thioalkyl or thioaryl radical of the formula

where Y is a branched or unbranched aliphatic group or an aromatic group which can also contain hetero atoms, and $R^E$ is a reactive group which is able to undergo bonding under mild conditions selectively with amino, carboxyl, thiol or other functional groups in substances of biological interest, and $A^\ominus$ is an anion which does not adversely affect the chemiluminescence.

It has now emerged that special acridinium derivatives are particularly suitable, by reason of their outstanding stability and their unexpectedly high detection sensitivity, especially for use as chemiluminescent compounds.

Accordingly, the invention relates to chemiluminescent acridinium derivatives of the formula I

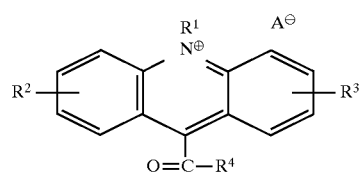

in which $R^1$ is hydrogen, an alkyl, alkenyl or alkynyl radical having 1 to 10 carbon atoms, or a benzyl or aryl group, $R^2$ and $R^3$ are hydrogen, an alkyl group having 1 to 4 carbon atoms, a substituted or unsubstituted amino group, a carboxyl, alkoxy, cyano or nitro group, or halogen, $R^4$ represents a radical of the formula II or III

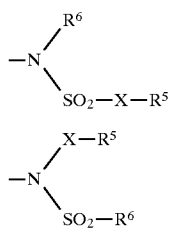

(II)

(III)

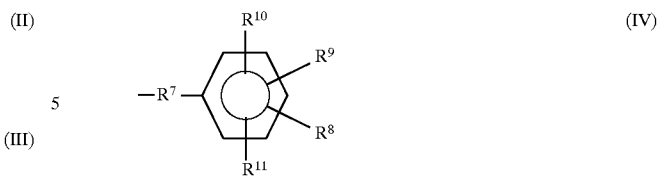

(IV)

in which $R^5$ is a reactive group which is able to undergo bonding under mild conditions selectively with amino, carboxyl, thiol or other functional groups in substances of biological interest, $R^6$ is hydrogen, an alkyl, alkenyl or alkoxy radical having 1 to 10 carbon atoms, a substituted amino group, a benzyl group, an aryl group, a heteroalkyl group or a heterocycle, each of which can also be substituted by hydroxyl, amino, alkylamino, alkyl, alkenyl or alkoxy having 1 to 4 carbon atoms, polyalkoxy or aryloxy groups or a heterocyclic group, it being possible for the last-mentioned substituents in turn to be substituted by a heterocyclic compound or an amine, or together to form a heterocycle having O and/or S and/or NH or N-alkyl, and X denotes an arylene group which is bonded to the nitrogen or sulfur atom directly or via an alkylene or oxyalkylene group and is bonded to the radical $R^5$ via an alkylene or oxyalkylene group and which can also be substituted one or more times by alkyl, alkenyl, hydroxyl, amino, alkoxy, polyalkoxy or aryloxy groups and/or hetero atoms, or denotes the radical of an aliphatic, araliphatic or aromatic, not necessarily natural, amino carboxylic acid, or is a phenylene group when $R^6$ is a phenyl group which is substituted one or more times by $C_1$–$C_6$-alkyl and the quaternary ammonium compounds.

The substances of biological interest are to be understood to include, in particular, antigens. This term covers, for example, hormones, steroids, pharmaceuticals, metabolites of pharmaceuticals, toxins, alkaloids and even antibodies.

Examples of suitable aminocarboxylic acids are glycine, alanine, serine, phenylalanine, histidine, α-aminobutyric acid, methionine, valine, norvaline, leucine, iso-leucine, norleucine, aspartic acid, glutamic acid, 4-aminobenzoic acid, 4-aminophenylacetic acid, 4-aminophenoxyacetic acid and 3-(4-amino)phenylpropionic acid.

The anion which does not adversely affect the chemiluminescence can be, for example, a tetrafluoroborate, perchlorate, halide, alkylsulfate, halosulfonate, alkylsulfonate or arylsulfonate anion. It is also possible for any other anion to be employed as long as it does not quench or diminish the chemiluminescence.

The heteroalkyl groups or heterocyclic groups preferably contain hetero atoms which can contribute to increasing the solubility of the compounds according to the invention in water, such as, for example, nitrogen, oxygen, sulfur, phosphorus or combinations thereof. Examples of particularly suitable heterocycles are morpholine, piperazine, piperidine, tetrahydrofuran, dioxanes etc.

Particularly important acridinium derivatives are those which are claimed in claim 1 and in which X is a group of the formula IV in which $R^7$ is a substituent of the formula $-(CH_2)_n-$ or $((CH_2)_m-O)_n-$, with n=0 to 4 and m=1 to 6, $R^8$ is a substituent in the ortho, meta or para position to $R^7$ of the formula $-(CH_2)_p-$, a polyalkylene oxide group of the formula $-(O-(CH_2)_m-)_p$ or $-((CH_2)_m-O-)_p$, preferably with p=1–6 and m=1–6, or a branched or unbranched hydrocarbon radical having 1–4 carbon atoms, and the substituents $R^9$–$R^{11}$ are hydrogen or straight-chain or branched hydrocarbon radicals having up to 30 carbon atoms, it also being possible for one or more $-CH_2-$ units to be replaced by O, S, SO, $SO_2$, NH or N—alkyl, and for two of these substituents to be linked to form a ring.

Particularly important for the possibilities of employing the acridinium derivatives according to the invention is the substituent $R^5$. Suitable choice of this group results in the acridinium derivative having a reactivity which is so high that it is able to undergo bonding even under mild conditions selectively with a functional group of the biological substance which is to be detected. Suitable reactive groups are shown in the list which follows:

a)

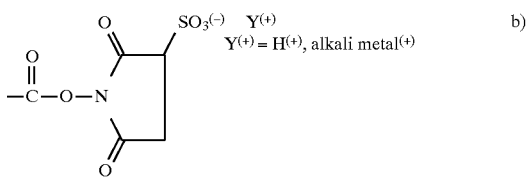

b)

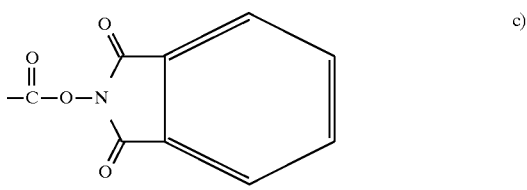

c)

d)

e)

f)

g)

-continued h) 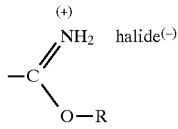

i) 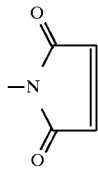

k) 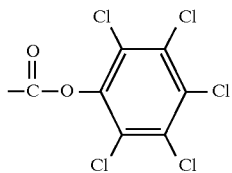

l) 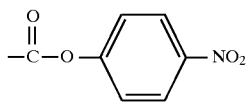

m) 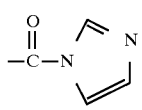

n) 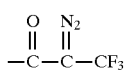

o) 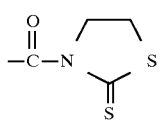

In many cases, acridinium derivatives according to the invention which have proven suitable are those in which $R^5$ is a group of the formula V

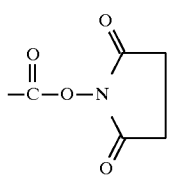
(V)

Furthermore, acridinium compounds of the formula VI have proven to be particularly suitable. Formula VI is

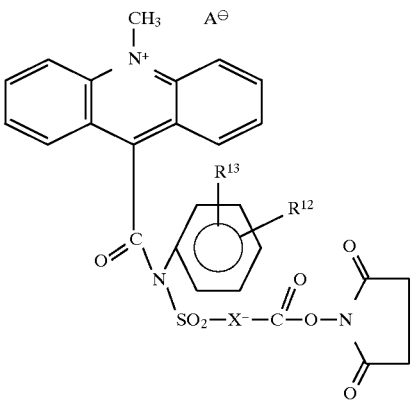
(VI)

in which X is a group of the formula VII

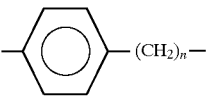
(VII)

with n=2 or 4,
and $R^{12}$ and $R^{13}$ are, independently of one another, hydrogen, an alkyl group, an alkoxy group having 1–4 carbon atoms, a (—O—$CH_2$—$CH_2$)$_n$—OR group, where n has the meaning 0–8 and R is a morpholinoethyl or an alkyl group having 1–4 carbon atoms or an N,N-dimethylamino-ethyl group,
or are together an ethylenedioxy group, and $A^\ominus$ has the meanings mentioned in claim 1. These compounds are products which are readily soluble in water.

Among the Last-mentioned compounds of the formula VII, those which are in turn very particularly preferred are those in which X is a p-ethylenephenyl group, $R^{12}$=H and $R^{13}$ is a p-methoxy group, or $R^{12}$ is an ortho-methoxy and $R^{13}$ is a para-methoxy group, or $R^{12}$ and $R^{13}$ are together a 3,4-ethylenedioxy group, such as, for example, the compounds of the formula

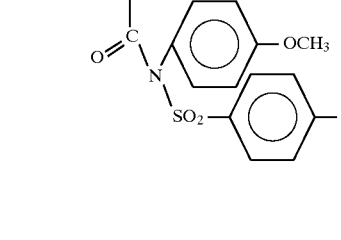

Further particularly suitable acridinium derivatives have the formula VIII

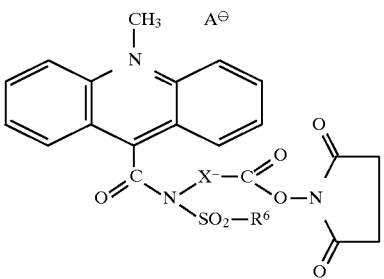
(VIII)

in which $R^6$ is an alkyl group having 1–4 carbon atoms or a phenyl group which can be substituted by up to three alkyl or alkoxy groups, each having 1–4 carbon atoms, by a —(—O—$CH_2$—$CH_2$)$_n$—OR group, where n has the meaning 0–8 and R is a morpholinoethyl or an N,N-dimethylamino-ethyl group or alkyl group having 1–4 carbon atoms, or by an ethylenedioxy group, and X has the meanings mentioned in claim 1 or 2, or in which $R^6$ is a phenyl group which can be substituted by up to three alkyl groups each having 1–4 carbon atoms, and X— is an ortho-, meta- or para-phenylene group. These compounds are also products which are readily soluble in water.

It is surprising that acridinium-9-carboxamides substituted by sulfonyl on the amide nitrogen exhibit excellent chemiluminescence, because it is known that, in contrast to the acridinium-9-carboxylic esters, acridinium-9-carboxamides show no chemiluminescence whatever (cf. F. McCapra in W. Carruthers and J. K. Sutherland: Progress in Organic Chem., Vol. 8, 231–277, 1973, Butterworth, London).

A significant advantage of the acridinium compounds according to the invention compared with the acridinium phenyl esters disclosed in European Patent Application 82,636 lies in the considerably more rapid reaction kinetics of light emission (cf. P 36 28 573.0).

Another advantage is provided by the stability of the tracers prepared with the aid of the compounds according to the invention. FIG. 1 shows the result of a stability test in which the intensity of the particular chemiluminescence signal was measured after storage at elevated temperature (50° C.). Curve 1 relates to tracers prepared from the compound a) N-(4-methoxyphenyl)-N-[4-(2-succinimidyloxycarbonylethyl)benzenesulfonyl]-10-methylacridinium-9-carboxamide fluorosulfonate (6), curve b) relates to tracers prepared from the compound N-(4-methoxyphenyl)-N-[4-(4-succinimidyloxycarbonylbutyl)-benzenesulfonyl]-10-methylacridinium-9-carboxamide fluorosulfonate (11) and curve c) relates to the tracers prepared from the compound 4-(2-succinimidyloxycarbonyl-ethyl)phenyl-10-methylacridinium-9-carboxylate methosulfate (European Patent Application 82,636, page 10).

It is clearly evident that the tracers, according to the invention, from the compounds a) and b) are more stable than the corresponding compounds from c).

A similar result is obtained in a corresponding test at 4° C. FIG. 2 shows the signal intensity after storage at 4° C. Once again, the tracer prepared from compound a) proves to be distinctly more stable than that prepared from compound c).

The acridiniumsulfonamide derivatives according to the invention can be prepared starting from acridine-9-carbonyl chloride (IX). To prepare the latter, for example acridine is reacted with potassium cyanide in ethanol/glacial acetic acid by the method indicated by Lehmstedt and Hundertmark in Ber. 63, 1229 (1930) to give 9-cyanoacridine. From this is obtained, preferably after recrystallization, by reaction with sulfuric acid and sodium nitrite by the method described by Lehmstedt and Wirth in Ber. 61, 2044 (1928), acridine-9-carboxylic acid. Reaction of acridine-9-carboxylic acid with, for example, thionyl chloride results in the compound of the formula IX

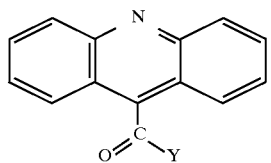

(IX)

in which Y has the meaning of chlorine. It is also possible, in place of a halogen, to introduce for Y in the compound IX a hydroxycarbonylalkyl, hydroxycarbonylaryl or imidazolide group.

The acid chloride (IX) can then be reacted with a protected sulfonamide carboxylic acid of the formula X

or of the formula XI

in which X and $R^6$ have the abovementioned meanings, and Z is a radical which protects the carboxyl group and is subsequently eliminated. It is possible to employ for this reaction, for example, N-(4-benzoxycarbonylphenyl)-N-4-toluenesulfonamide. It is advantageous to use the t-butyl esters, whose protective group can be introduced and eliminated again under particularly mild conditions. The acid produced after elimination of the protective groups is then converted, using a suitable compound, for example using N-hydroxysuccinimide, into the radical $R^5$. From this is obtained the chemiluminescent acridine compound by alkylation on the nitrogen in the 10-position.

The resulting acridinium compounds can then be reacted with a substance of biological interest, for example an antigen, an antibody, a hormone, a pharmaceutical, a metabolite of a pharmaceutical, a toxin or an alkaloid, to give a luminescent compound. This entails the acridinium derivative being bonded either directly or via a bridging molecule, such as, for example, amino acids, oligo- or polyamino acids, peptides or synthetic polymers, to the biologically interesting substance, with the formation of a stable immunologically active conjugate. This conjugate is also called tracer and is employed in the luminescence immunoassays described hereinafter. Required for the luminescence immunoassay according to the invention for the determination of an antigenic substance in a liquid sample by a competitive or a sandwich method is at least one immunologically active component which is immobilized on a solid phase, and, in addition, the luminescent tracer.

After the immunological reaction and any washing steps which are required are complete, the light emission is initiated by successive or simultaneous addition of one or more reagents, with at least one reagent containing an oxidizing agent in bound or unbound form. It is now possible to carry out the luminescence immunoassay in a variety of ways.

One possibility comprises incubation of the immobilized antibody, which reacts specifically with the antigen, with a sample of the liquid which is to be investigated, and with a conjugate composed of the antigen and of a chemiluminescent acridinium derivative (antigen tracer), separation of the sample and the unbound tracer, contacting the bound tracer with the reagents necessary to bring about light emission, and then determination of the amount of antigen present from the measured intensity of light emission.

Another possibility for carrying out the luminescence immunoassay comprises incubation of an immobilized antibody, which reacts specifically with the antigen, with a sample of the liquid which is to be investigated and with a conjugate composed of a second specifically reacting antibody and of a chemiluminescence acridinium derivative, separation of the sample and the unbound conjugate with marker, contacting the bound conjugate with marker with the reagents necessary to bring about light emission, and determination of the amount of antigen present from the measured intensity of light emission.

The abovementioned luminescence immunoassays can also be carried out in such a way that the liquid which is to be investigated is separated from the immobilized antibody before the addition of the conjugate with marker.

In another Luminescence immunoassay which can be carried out according to the invention, it is not the antibody but the antigen which is immobilized. Thus, it is possible for an immobilized antigen, which reacts specifically with the antibody, to be incubated with a sample of the liquid which is to be investigated and with a solution of a conjugate composed of the antibody and of a chemiluminescent acridinium derivative, and for the sample and the unbound conjugate with marker then to be separated, and then the bound conjugate with marker then to be contacted with the necessary reagents. Light emission then occurs, and the amount of antigen present can be determined from the intensity thereof.

Another variant comprises incubation of an immobilized antigen, which reacts specifically with the antibody, with a solution of a conjugate composed of the antibody and of a chemiluminescent acridinium derivative, separating off the unreacted conjugate with marker, addition of a sample of the liquid which is to be investigated, subsequently separating off the sample again, contacting the bound conjugate with marker with the reagents necessary to bring about light emission, and then determination from the latter of the amount of antigen present.

Finally, the luminescence immunoassay can also be carried out in such a way that an immobilized antigen, which reacts specifically with the antibody, is incubated with a solution of a conjugate composed of the antibody and of a chemiluminescent acridinium derivative, a sample of the liquid which is to be investigated is added, the sample and the unbound conjugate are separated, the bound conjugate with marker is contacted with the necessary reagents, and then the amount of antigen present is determined from the measured light emission.

The preparation of the acridinium compounds according to the invention is explained in detail in Examples 1 to 7.

EXAMPLE 1
N-(4-Methoxyphenyl)-N-[4-(2-benzyloxycarbonylethyl)-benzenesulfonyl]acridine-9-carboxamide (3)

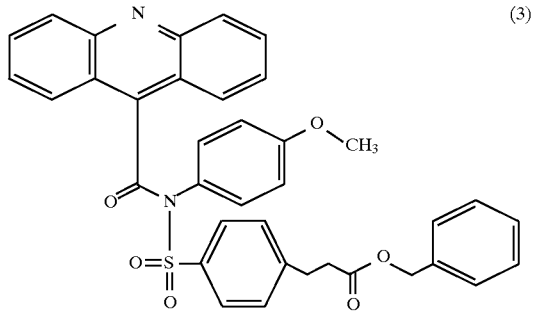

(3)

460 mg of 4-(N,N-dimethylamino)pyridine and 22.1 ml of triethylamine are added to 17 g of benzyl 4'-[N-(4-methoxyphenyl)sulfamido]-3-phenylpropionate (1) in 400 ml of dichloromethane and, after 10 min, 11.12 g of acridine-9-carbonyl chloride hydrochloride (2) are added, and the mixture is refluxed for 6 hours. The cooled solution is briefly stirred with 2N NaOH, and the organic phase is separated off, washed with $H_2O$, dried over magnesium sulfate and concentrated. The residue is purified by column chromatography.

Yield: 60% Melting point: 130°–132° C. NMR (DMSO, 100 MHz): δ=2.7–3.0 ppm (d,br,2H), δ=3.0–3.3 ppm (d,br,2H), δ=3.5 ppm (s,br,3H), δ=5.1 ppm (s,2H), δ=6.5 ppm (d,br, 2H), δ=7.1 ppm (d,br,2H), δ=7.35 ppm (s,5H), δ=7.5–8.3 ppm (m,12H).

N-(4-Methoxyphenyl)-N-[4-(2-carboxyethyl) benzenesulfonyl]-acridine-9-carboxamide hydrobromide (4)

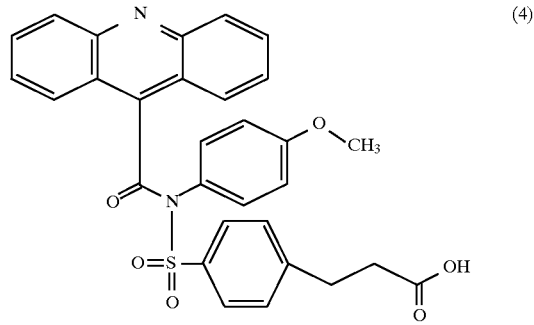

(4)

6.3 g of (3) in 30 ml of 33% HBr/glacial acetic acid are heated at 60° C. for 2 hours and, after cooling, 60 ml of diisopropyl ether are added, and the precipitate is filtered off with suction and dried in vacuo:

Yield: 90% Melting point: decomposition 237° C. NMR (DMSO, 100 MHz): δ=2.7 ppm.(d,br,2H), δ=3.1 ppm (d,br, 2H), δ=3.5 ppm (s,br,3H), δ=6.5 ppm (d,br,2H), δ=7.0–8.4 ppm (m,15H)

N-(4-Methoxyphenyl)-N-[4-(2-succinimidyl oxycarbonylethyl)-benzenesulfonyl]acridine-9-carboxamide (5)

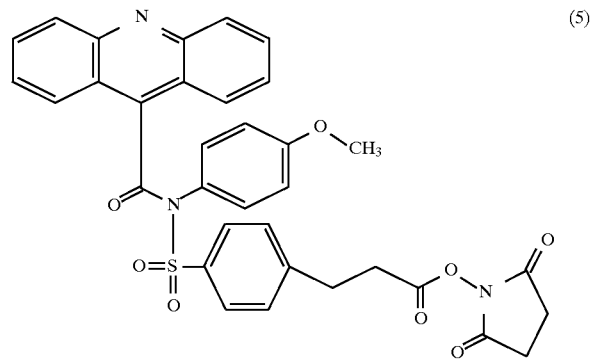

(5)

1.41 ml of triethylamine are added to 3.1 g of (4) in 50 ml of tetrahydrofuran, the mixture is cooled to −20° C., and 0.474 ml of ethyl chloroformate is added. Afterstirring for 20 min, 575 mg of N-hydroxysuccinimide are added, and the mixture is stirred at −20° C. for 3 hours and left to reach room temperature overnight while stirring. The precipitate is filtered off with suction, thefiltrate is concentrated, the residue is taken up in dichloromethane or ethyl acetate, and the resulting solution is washed with water, $NaHCO_3$ solution and water and dried over $MgSO_4$. The organic phase is concentrated, and the residue is recrystallized from toluene.

Yield: 50% NMR (DMSO, 100 MHz): δ=2.8 ppm (s,4H), δ=3.2 ppm (s,br, 4H), δ=3.5 ppm (s,Br,3H), δ=6.5 ppm (d,br,2H), δ=7.2 ppm (d,br,2H), δ=7.6–8.4 ppm (m,12H) IR: 3400 $cm^{-1}$ (br), 3060, 2930, 1815(w), 1780(w), 1740(s), 1690(m), 1600(w), 1510(m), 1370(m), 1250(m), 1203(m), 1175(m).

N-(4-Methoxyphenyl)-N-[4-(2-succinimidyloxycarbonylethyl)-benzenesulfonyl]-10-methylacridinium-9-carboxamide fluorosulfonate (6)

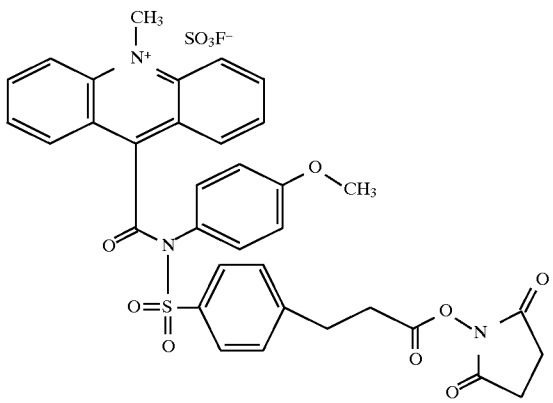

0.4 ml of methyl fluorosulfonate is added at −20° C. to 1.27 9 of (5) in 60 ml of dichloromethane. The mixture is left to stir at −20° C. for 2 hours and to reach room temperature overnight. Addition of toluene results in precipitation of a yellow solid which is filtered off with suction and dried in vacuo.

Yield: 80% NMR (DMSO, 100 MHz): δ=2.9 ppm (s,4H), δ=3.2 ppm (s,br, 4H), δ=3.5 ppm (s,br,3H), δ=4.8 ppm (s,br,3H), δ=6.5 ppm (br,2H), δ=7.2 ppm (br,2H), δ=7.6–9.0 ppm (m,12H) IR=3400 cm$^{-1}$ (br), 3160, 2970, 1810(w), 1785(w), 1740(s), 1695(m), 1600(w), 1555(w), 1510(m), 1370(m), 1290(m), 1250(m), 1210(m), 1170(m) Mass spectrum: m/z: 652 M$^+$ (cation)

EXAMPLE 2

The preparation of N-(4-methoxyphenyl)-N-[4-(4-succinimidyloxycarbonylbutyl)benzenesulfonyl]-10-methylacridinium-9-carboxamide fluorosulfonate (11) starting from benzyl 4'-[N-(4-methoxyphenyl)sulfamido]-5-phenylvalerate(7) and acridine-9-carbonyl chloride hydrochloride (2) is carried out in analogy to the synthesis of (6). The yields in the individual steps in the synthesis, and the spectroscopic characterization are indicated hereinafter.

N-(4-Methoxyphenyl)-N-[4-(4-benzyloxycarbonylbutyl)-benzenesulfonyl]acridine-9-carboxamide (8)

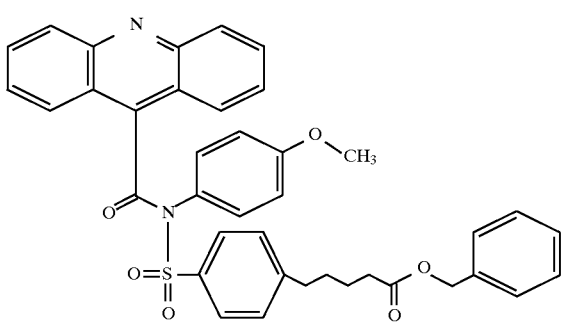

Yield: 40% viscous oil, partially solidifies NMR (CDCl$_3$, 100 MHz): δ=2.85 (m,4H), δ=2.45 ppm (t, br,2H), δ=2.8 ppm (t,br,2H), δ=3.5 ppm (s,3H), δ=5.15 ppm (s,2H), δ=6.3 ppm (d,2H), δ=6.9 ppm (d,2H), δ=7.3–8.3 ppm (m,17H).

N-(4-Methoxyphenyl)-N-[4-(4-carboxybutyl)benzenesulfonyl]-acridine-9-carboxamide hydrobromide (9)

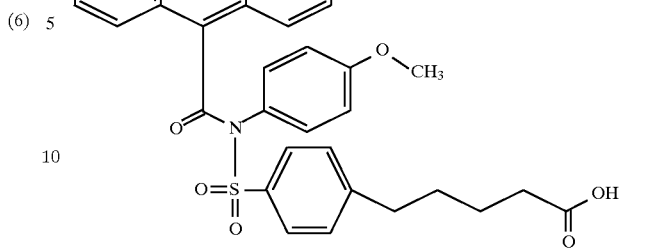

Yield: 95% Melting point: decomposition 153°–5° C. NMR (DMSO, 100 MHz): δ=1.7 ppm (s,br,4H), δ=2.3 ppm (t,br, 2H), δ=2.8 ppm (s,br,2H), δ=3.5 ppm (s,br,3H), δ=6.5 ppm (br,2H), δ=7.05 ppm (br,2H), δ=7.5–8.5 ppm (m,12H).

N-(4-Methoxyphenyl)-N-[4-(4-succinimidyloxycarbonylbutyl)-benzenesulfonyl]acridine-9-carboxamide (10)

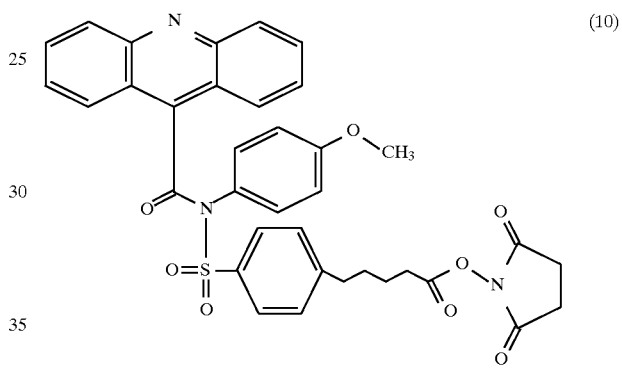

Yield: 25% Melting point: decomposition 75°–80° C. NMR (DMSO, 100 MHz): δ=1.8 ppm (br,4H), δ=2.3 ppm (s, 2H), δ=2.85 ppm (s,br,6H), δ=3.5 ppm (s,br,3H), δ=6.5 ppm (d,br,2H), δ=7.05 ppm (d,br,2H), δ=7.5–8.3 ppm (m,12H)

N-(4-Methoxyphenyl)-N-[4-(4-succinimidyloxycarbonylbutyl)-benzenesulfonyl]-10-methylacridinium-9-carboxamide fluorosulfonate (11)

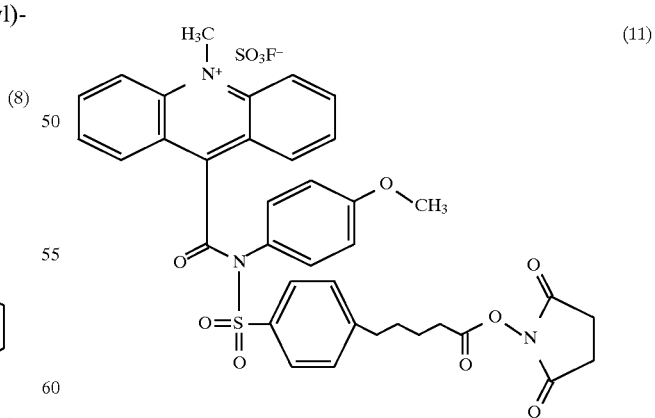

Yield: 90% NMR (DMSO, 100 MHz): δ=1.8 ppm (br,4H), δ=2.3 ppm (s, br,2H), δ=2.8 ppm (s,br,6H), δ=3.5 ppm (s,br,3H), δ=4.8 ppm (br,3H), δ=6.5 ppm (br,2H), δ=7.05 ppm (br, 2H), δ=7.5–9.0 ppm (m,12H) IR: 3340 cm$^{-1}$ (br), 3060(w), 2930(m), 2870(w), 1810(w), 1785(w), 1740(s), 1695(m), 1600(w), 1550(w), 1510(m), 1460(w), 1370(m), 1290(s), 1250(s), 1205(s), 1170(s) Mass spectrum: m/z=680 M⁺(cation)

EXAMPLE 3

The preparation of N-(2,4-dimethoxyphenyl)-N-[4-(2-succinimidyloxycarbonylethyl)benzenesulfonyl]-10-methyl-acridinium-9-carboxamide fluorosulfonate (16a) starting from benzyl 4'-[N-(2,4-dimethoxyphenyl) sulfamido]-3-phenylpropionate (12a) and acridine-9-carbonyl chloride hydrochloride (2) is carried out in analogy to the synthesis of (6). The yields in the individual steps in the synthesis, and the spectroscopic characterization are indicated hereinafter.

N-(2,4-Dimethoxyphenyl)-N-[4-(2-benzyloxycarbonylethyl)-benzenesulfonyl]acridine-9-carboxamide (13a)

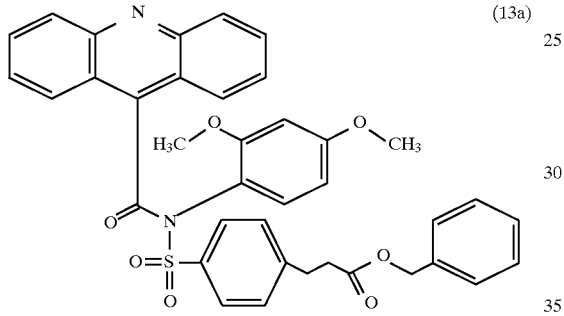

Yield: 50% Melting point: 74° C. NMR (DMSO, 100 MHz): δ=2.9 ppm (d,br,2H), δ=3.1 ppm (d,br,2H), δ=3.3 ppm (s,3H), δ=3.4 ppm (s,3H), δ=5.1 ppm (s,2H), δ=5.9–6.2 ppm (m,2H), δ=7.0 ppm (d,1H), δ=7.35 ppm (s,5H), δ=7.5–8.2 ppm (m,12H)

N-(2,4-Dimethoxyphenyl)-N-[4-(2-carboxyethyl)benzenesulfonyl]acridine-9-carboxamide hydrobromide (14a)

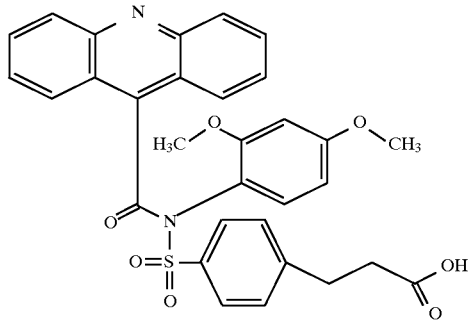

Yield: 95% NMR (DMSO, 100 MHz): δ=2.75 ppm (d,br, 2H), δ=3.05 ppm (d,br,2H), δ=3.3 ppm (s,3H), δ=3.5 ppm (s,3H), δ=5.95–6.3 ppm (m,2H), δ=7.05 ppm (d,1H), δ=7.6–8.6 ppm (m, 12H), δ=9.2 ppm (s,br,2H).

N-(2,4-Dimethoxyphenyl)-N-[4-(2-succinimidyl oxycarbonyl-ethyl)benzenesulfonyl]acridine-9-carboxamide (15a)

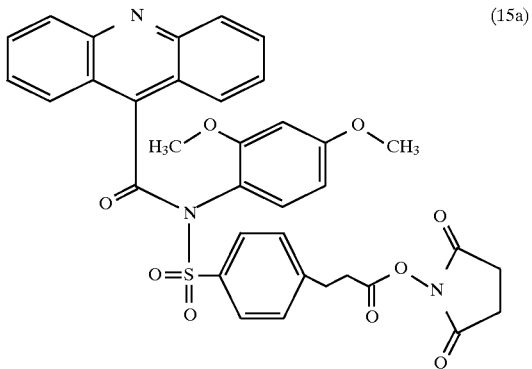

Yield: 45% Melting point: –105° C. decomposition NMR (DMSO, 100 MHz): δ=2.9 ppm (s,4H), δ=3 ppm (br,2H), δ=3.2 ppm (s,3H), δ=3.4 ppm (s,3H), δ=5.9–6.3 ppm (m,2H), δ=7.0 ppm (d,1H), δ=7.5–8.4 ppm (m,12H) IR (KBr disk): 3440 cm⁻¹ (br), 3060 (w), 2930(w), 2850(w), 1815(w), 1785(w), 1740(s), 1695(m), 1600(w), 1510(m), 1460(w), 1440(w), 1365(m), 1320(w), 1290(w), 1240(m), 1210(s), 1165(m), 1085(m)

N-(2,4-Dimethoxyphenyl)-N-[4-(2-succinimidyl oxycarbonyl-ethyl)benzenesulfonyl]-10-methylacridinium-9-carboxamide fluorosulfonate (16a)

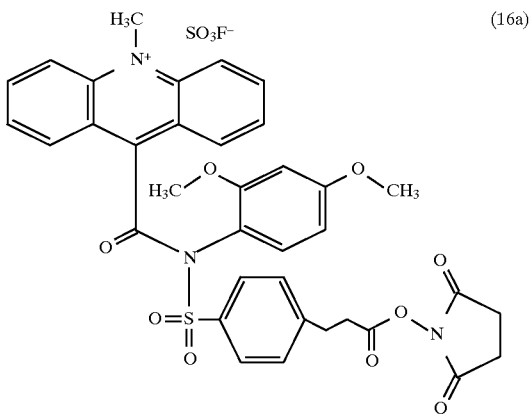

Yield: 80% Melting point: –135° C. decomposition NMR (DMSO, 100 MHz): δ=2.9 ppm (s, 4H), δ=2.95–4.2 ppm (m 10H), δ=4.8–5.0 ppm (s,s,3H), δ=6.05–6.25 ppm (m,1H), δ=7.6–9.0 ppm (m,14H) IR (KBr disk): 3430 cm⁻¹(m), 2950(w), 2870(w), 2825(w), 1810(w), 1780(m), 1750(s), 1695(m), 1610(m), 1555(w), 1510(m), 1465(m), 1380(m), 1285(m), 1250(m), 1210(s), 1170(m)

EXAMPLE 4

The synthesis of N-(3,4-ethylenedioxyphenyl)-N-[4-(2-succinimidyloxycarbonylethyl)benzenesulfonyl]-10-methyl-acridinium-9-carboxamide fluorosulfonate (16b) starting from benzyl 4'-[N-(3,4-ethylenedioxyphenyl) sulfamido]-3-phenylpropionate (12b) and acridine-9-carbonyl chloride hydrochloride (2) is carried out in analogy to Example 1. The yields in the individual steps and the spectroscopic characterization are indicated hereinafter.

N-(3,4-Ethylenedioxyphenyl)-N-[4-(2-benzyloxycarbonyl-ethyl)benzenesulfonyl]acridine-9-carboxamide (13b)

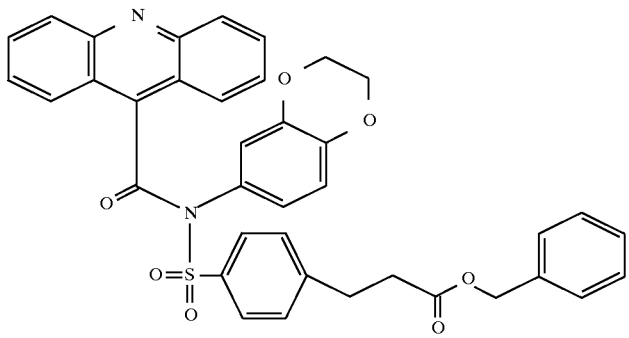
(13b)

Yield: 50% Melting point: 91.5° C. NMR (DMSO, 100 MHz): δ=2.9 ppm (d,br,2H), δ=3.1 ppm (d, br,2H), δ=4.0 ppm (s,Br,4H), δ=5.1 ppm (s,2H), δ=6.3–6.8 ppm (m,3H), δ=7.3 ppm (s,5H), δ=7.6–8.3 ppm (m,12H).

N-(3,4-Ethylenedioxyphenyl)-N-[4-(2-carboxyethyl)-benzenesulfonyl]acridine-9-carboxamide hydrobromide (14b)

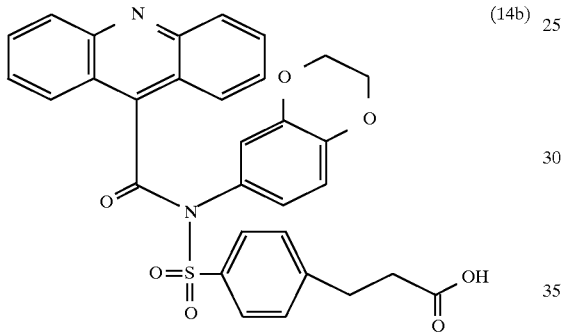
(14b)

Yield: 95% Melting point: >200° C. NMR (DMSO, 100 MHz): δ=2.7 ppm (m,2H), δ=3.05 ppm (m, 2H), δ=4.0 ppm (s,br,4H), δ=6.3–6.8 ppm (m,3H), δ=7.5–8.6 ppm (m,12H), δ=9.6 ppm (s,br,2H).

N-(3,4-Ethylenedioxyphenyl)-N-[4-(2-succinimidyloxy-carbonylethyl)benzenesulfonyl]acridine-9-carboxamide (15b)

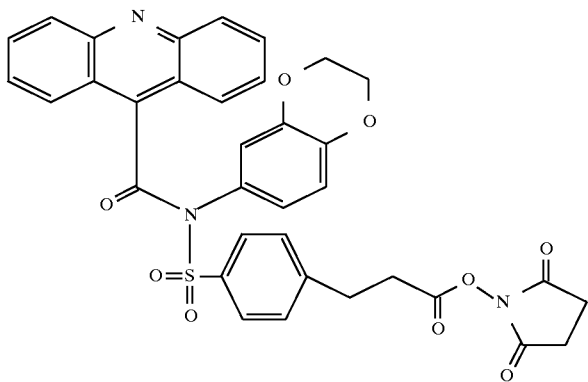
(15b)

Yield: 45% Melting point: 140° C. decomposition NMR (DMSO, 100 MHz): δ=2.7–2.9 ppm (d,s, overlapping, 6H), δ=3.0 ppm (d,2H), δ=4.0 ppm (s,br,4H), δ=6.3–6.8 ppm (m,3H), δ=7.5–8.4 ppm (m,12H) IR(KBr disk): 3420 cm$^{-1}$ (br), 3060(m), 2980(m), 2930(m), 1810(w), 1790(w), 1740 (m), 1695(s), 1590(m), 1460(w), 1430(w), 1410(w), 1370 (m), 1300(m), 1225(s), 1175(s).

N-(3,4-Ethylenedioxyphenyl)-N-[4-(2-succinimidyloxy-carbonylethyl)benzenesulfonyl]-10-methyl acridinium-9-carboxamide fluorosulfonate (16b)

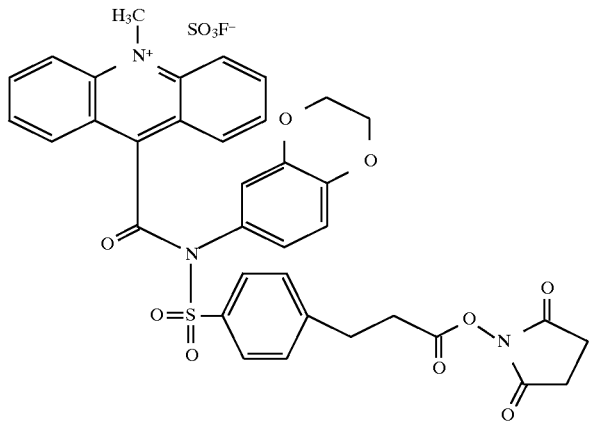

(16b)

Yield: 80% Melting point: –110° C., decomposition NMR (DMSO, 100 MHz): δ=2.85 ppm (s,4H), δ=3.0–3.3 ppm (s,s,br,4H), δ=3.8–4.5 ppm (m,br,4H), δ=4.75–5.1 ppm (s, br with shoulder, 3H), δ=6.3–9.0 ppm (m,15H).

EXAMPLE 5

N-(4-Carboxyphenyl)-4-toluenesulfonamide (5-1)

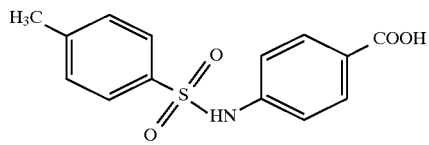

(5-1)

A mixture of 190.5 g (1 mole) of 4-toluenesulfonyl chloride in 300 ml of i-propyl ether is added dropwise at 20°–30° C. to one of 252 g (3 mole) of sodium bi-carbonate and 139.1 g (1 mole) of 4-aminobenzoic acid in 2.5 l of water. The mixture is stirred vigorously for 2–4 hours, until the sulfonyl chloride has been consumed. The aqueous solution is separated off and then adjusted to pH 1 with concentrated hydrochloric acid, and the precipitate is taken up in propyl acetate. The extract is washed 2× with 2N hydrochloric acid and 1× with water, dried over sodium sulfate and evaporated. 240 g (82.5% of theory) of N-(4-carboxyphenyl)-4-toluenesulfonamide are obtained.

$^1$H NMR (DMSO-$d_6$): δ=2.3 (s; $CH_3$); 7.1 d, aromatic, 2H) 7.3 (d, aromatic, 2H); 7.6–7.9 (m, aromatic, 4H); 10.75 (broad); 12.7 (broad).

N-(4-Benzyloxycarbonylphenyl)-4-toluenesulfonamide (5-2)

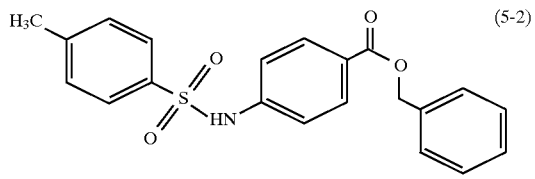

(5-2)

A solution of 11.64 g (40 mmol) of N-(4-carboxyphenyl)-4-toluenesulfonamide, 5.06 g (40 mmol) of benzyl chloride and 5.20 g (44 mmol) of di-i-propylethylamine in 100 ml of dimethylformamide is heated at 140° C. for 4 hours. After the reaction is complete, the mixture is evaporated in vacuo, the residue is taken up in propyl acetate, and the solution is washed 2× with 2N hydrochloric acid and 2× with saturated $NaHCO_3$ solution, dried over sodium sulfate and evaporated. 11.8 g (78% of theory) of N-(4-benzyloxycarbonylphenyl)-4-toluenesulfonamide, which are recrystallized from methanol, are obtained.

$^1$H NMR (DMSO-$d_6$): δ=2.3 (s; $CH_3$); 5.3 (s, $CH_2$); 7.1–7.3 (dd, 4 aromatic H); 7.4 (s, $C_6H_5$); 7.7–7.9 (dd, 4 aromatic H); 10.8 (broad, NH).

N-(4-Benzyloxycarbonylphenyl)-N-(4-toluenesulfonyl)-acridine-9-carboxamide (5-3)

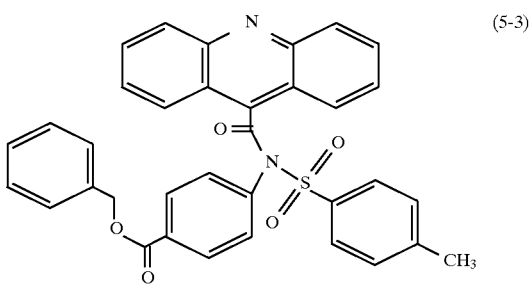

(5-3)

2.1 ml (15 mmol) of triethylamine in 10 mL of tetrahydrofuran are added dropwise at 25° C. to a solution of 1.5 g (4 mmol) of N-(4-benzyloxycarbonylphenyl)-4-toluenesulfonamide, 1.23 g (4.4 mmol) of acridinecarbonyl chloride hydrochloride and 0.02 g of dimethylaminopyridine in 20 ml of anhydrous tetrahydrofuran. The temperature is raised to 60° C. The product which has crystallized out is, after the reaction is complete, stirred with methanol, filtered off with suction and recrystallized from ethyl acetate.

Yield: 1.57 g (67.0% of theory) $^1$H NMR ($CDCl_3$): δ=2.5 (s, $CH_3$); 5.2 (s, $CH_2$); 7.3 (s, $C_6H_5$), 7.0–8.2 (m, 16 aromatic H).

N-(4-Carboxyphenyl)-N-(4-toluenesulfonyl)acridine-9-carboxamide hydrobromide (5-4)

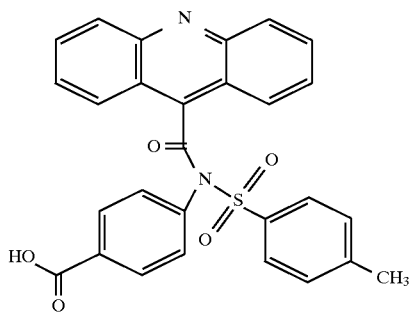

(5-4)

1.17 g (2 mmol) of N-(4-benzyloxycarbonylphenyl)-N-(4-toluenesulfonyl)acridine-9-carboxamide are stirred with 10 ml of 33% strength solution of hydrogen bromide in glacial acetic acid while heating at 60° C. for 4 hours. After cooling, the precipitate is filtered off with suction and dried in vacuo. Yield: 1.00 g (87% of theory)

$^1$H NMR (TFA): δ=2.6 (s, CH$_3$); 7.3–8.6 (m, 16 aromatic H); 11.65 (s, NH); MS: 496 (M$^+$).

N-(4-Succinimidyloxycarbonylphenyl)-N-(4-toluenesulfonyl)-acridine-9-carboxamide (5-5)

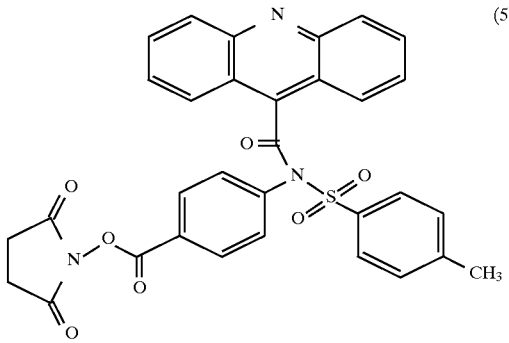

(5-5)

0.11 g (1 mmol) of ethyl chloroformate is added, while stirring at −15° C., to a solution of 0.57 g (1 mmol) of N-(4-carboxyphenyl)-N-(4-toluenesulfonyl)acridine-9-carboxamide hydrobromide and 0.21 g (2 mmol) of triethylamine in 25 ml of anhydrous tetrahydrofuran. The mixture is stirred at the same temperature for 1 hour and then 0.12 g (1 mmol) of N-hydroxysuccinimide is added. After a further hour, the mixture is Left to stand at room temperature for 15 hours. It is evaporated in vacuo, the residue is taken up in ethyl acetate, and the solution is washed with water, sodium bicarbonate solution and water and dried over sodium sulfate. Evaporation yields 0.42 g (70.8% of theory) of the desired product.

$^1$H NMR (TFA): δ=2.6 (s, CH$_3$), 3.1 (s, CH$_2$—CH$_2$), 7.0–8.6 (m, 16 aromatic H).

N-(4-Succinimidyloxycarbonylphenyl)-N-(4-toluenesulfonyl)-10-methylacridinium-9-carboxamide fluorosulfonate (5-6)

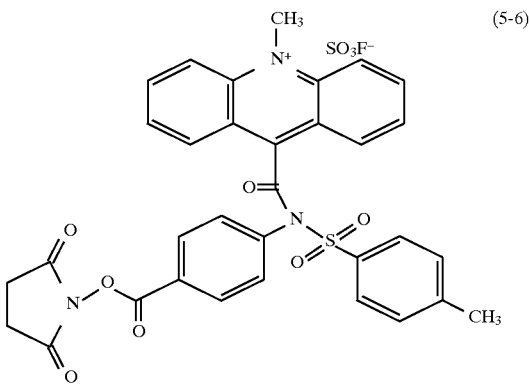

(5-6)

0.85 g (7.5 mmol) of methyl fluorosulfonate is added, while stirring at 25° C., to a solution of 0.59 g (1 mmol) of N-(4-succinimidyloxycarbonylphenyl)-N-(4-toluene-sulfonyl)acridine-9-carboxamide in 30 ml of 1,2-dichloroethane. The reaction product precipitates out within 4 hours. Filtration with suction and drying result in 0.43 g (60.8% of theory) of the desired product.

$^1$H NMR (TFA): δ=2.6 (s, Ar—CH$_3$); 3.1 (s, CH$_2$—CH$_2$); 4.9 (s, N—CH$_3$); 7.3–8.8 (m, 16 aromatic H).

EXAMPLE 6

N-(4-Succinimidyloxycarbonylmethylphenyl)-N-(4-toluene-sulfonyl)-10-methylacridinium-9-carboxamide fluorosulfonate is obtained from N-(4-carboxymethylphenyl)-4-toluenesulfonamide in the same way as in Example 5.

N-(4-Carboxymethylphenyl)-4-toluenesulfonamide (6-1)

$^1$H NMR (DMSO): δ=2.3 (s, CH$_3$); 3.5 (s, CH$_2$); 7.0 (AB, C$_6$H$_4$); 7.3–7.6 (AB; C$_6$H$_4$); 10.2 (s, NH).

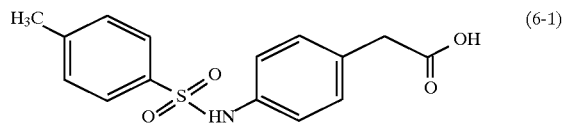

(6-1)

N-(4-Benzyloxycarbonylmethylphenyl)-4-toluenesulfonamide (6-2)

Yield: 35% of theory $^1$H NMR (DMSO): δ=2.3 (s, CH$_3$); 3.6 (s, COCH$_2$); 5.1 (s, OCH$_2$); 6.9–7.7 (m, 13 aromatic H); 10.2 (s, NH).

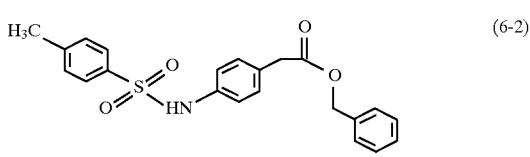

(6-2)

N-(4-Benzyloxycarbonylmethylphenyl)-N-(4-toluenesulfonyl)-acridine-9-carboxamide (6-3)

Yield: 35% of theory $^1$H NMR (CDCl$_3$): δ=2.55 (s, CH$_3$); 3.3 (s, COCH$_2$); 5.0 (s, O—CH$_2$), 6.7–8.2 (m, 21 aromatic H).

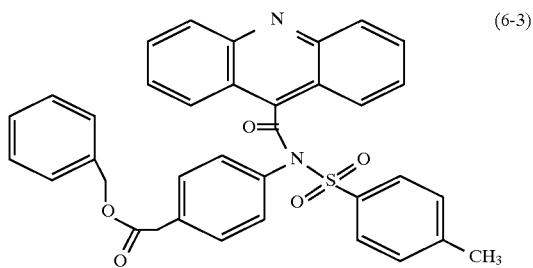
(6-3)

N-(4-Carboxymethylphenyl)-N-(4-toluenesulfonyl)acridine-9-carboxamide hydrobromide (6-4)

Yield: 95% of theory $^1$H NMR (TFA): δ=2.65 (s, CH$_3$); 3.55 (s,CH$_2$); 6.8–8.6 (m, 16 aromatic H)

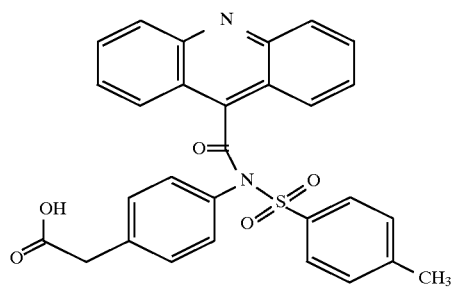
(6-4)

N-(4-Succinimidyloxycarbonylmethylphenyl)-N-(4-toluene-sulfonyl)acridine-9-carboxamide (6-5)

Yield: 71% of theory $^1$H NMR (TFA):d =2.65 (s, toluene-CH$_3$); 3.0 (s, CH$_2$—CH$_2$); 3.6 (broad, COCH$_2$); 6.9–8.5 (m, aromatic)

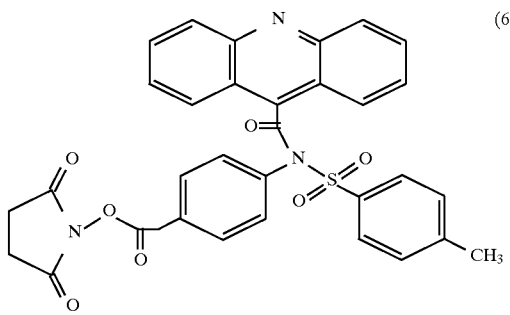
(6-5)

N-(4-Succinimidyloxycarbonylmethylphenyl)-N-(4-toluene-sulfonyl)-10-methylacridinium-9-carboxamide fluorosulfonate (6—6)

Yield: 80% of theory $^1$H NMR (TFA): δ=2.6 (s, toluene-CH$_3$); 2.9 (s, CH$_2$—CH$_2$); 3.6 (broad, COCH$_2$); 4.9 (s, N—CH$_3$); 6.8–8.9 (m, aromatic)

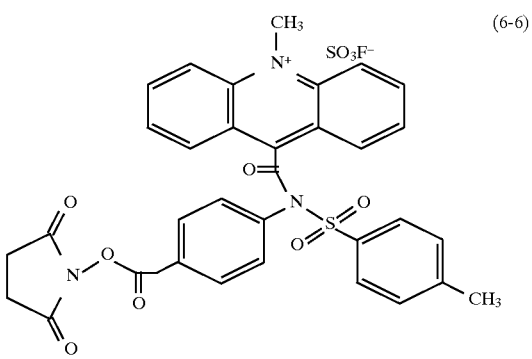
(6-6)

EXAMPLE 7

N-[4-(2-Succinimidyloxycarbonylethyl)phenyl]-N-(4-toluenesulfonyl)-10-methylacridinium-9-carboxamide fluorosulfonate is obtained from N-[4-(2-carboxyethyl)-phenyl]-4-toluenesulfonamide in the same way as in Example 5.

N-[4-(2-Carboxyethyl)phenyl]-4-toluenesulfonamide(7-1)

Yield: 44% of theory $^1$H NMR (DMSO): δ=2.3 (s, CH$_3$); 2.4–2.8 (m, CH$_2$—CH$_2$); 7.0 (AB, 4H); 7.2–7.8 (AB, 4H); 10.1 (s, NH).

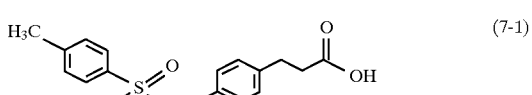
(7-1)

N-[4-(2-Benzyloxycarbonylethyl)phenyl]-4-toluenesulfonamide (7-2)

Yield: 78% of theory $^1$H NMR (CDCl$_3$): δ=2.35 (s, CH$_3$); 2.4–3.0 (m, CH$_2$—CH$_2$); 5.1 (s, O—CH$_2$); 7.0–7.8 (13 aromatic H, NH)

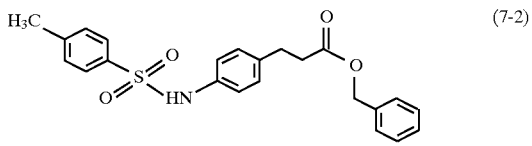
(7-2)

N-[4-(2-Benzyloxycarbonylethyl)phenyl]-N-(4-toluenesulfonyl)acridine-9-carboxamide (7-3)

Yield: 77% of theory $^1$H NMR (CDCl$_3$): δ=2.2–2.8 (m, 7H); 5.0 (s, CH$_2$); 6.65–7.0 (AB, 4 aromatic H); 7.3–8.3 (m, 17 aromatic H)

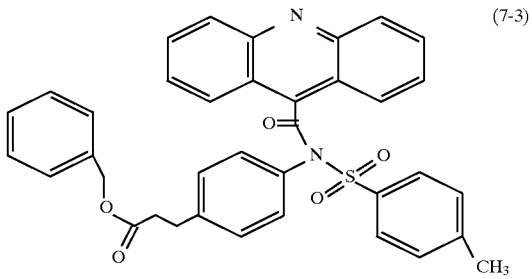
(7-3)

N-[4-(2-Carboxyethyl)phenyl]-N-(4-toluenesulfonyl)-acridine-9-carboxamide hydrobromide (7-4)

Yield: 65% of theory $^1$H NMR (CD$_3$OD): δ=2.1–2.8 (m, CH$_2$—CH$_2$); 2.5 (s, CH$_3$); 6.7–8.5 (16 aromatic H)

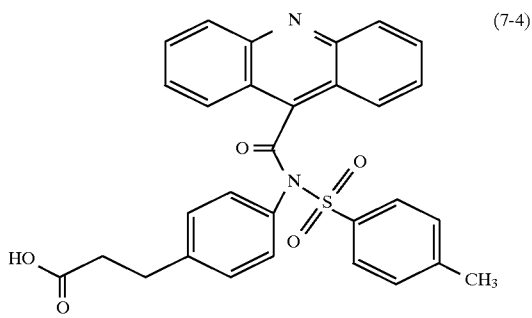

(7-4)

N-[4-(2-Succinimidyloxycarbonylethyl)phenyl]-N-(4-toluene-sulfonyl)acridine-9-carboxamide (7-5)
Yield: 90% of theory $^1$H NMR (CDCl$_3$): δ=2.6 (s, CH$_3$); 2.7 (broad, CH$_2$—CH$_2$); 2.8 (s, CH$_2$—CH$_2$); 6.6–8.3 (16 aromatic H)

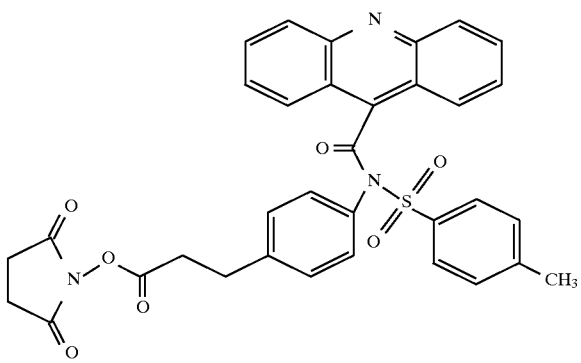

(7-5)

N-[4-Succinimidyloxycarbonylethyl)phenyl]-N-(4-toluenesulfonyl)-10-methylacridinium-9-carboxamide fluorosulfonate. (7-6)
Yield: 84% of theory $^1$H NMR (TFA): δ=2.6 (s, CH$_3$); 2.3–3.3 (broad background, 11H; s,3.1); 4.9 (S, N—CH$_3$); 6.7–8.8 (16 aromatic H)

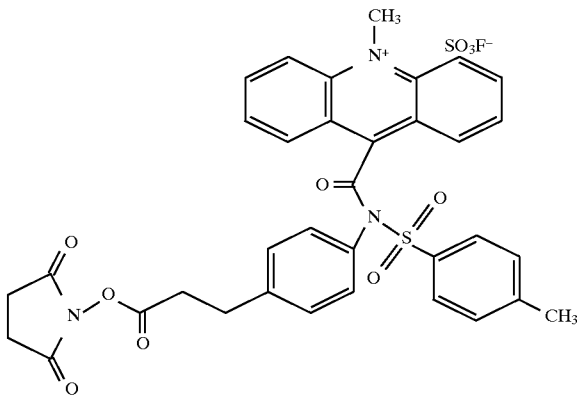

(7-6)

EXAMPLE 7a

N-[4-(N-Methylmorpholino-N-2-ethoxy)phenyl]-N-[4-(2-succinimidyloxycarbonylethyl)phenylsulfonyl ]-10-methylacridine-9-carboxamide diium difluorosulfonate is obtained in a manner analogous to that in the previous examples. Differing steps in the process are described in the following reaction stages.

3-(4-Chlorsulfonylohenyl)-propionic acid-tert.-butylester (7-a1)

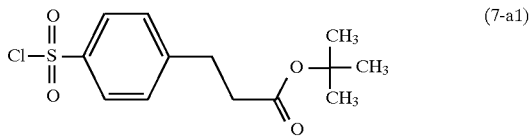

(7-a1)

25 g (0.1 mole) of 3-(4-chlorosulfonyl-phenyl)-propionic acid, 12 ml of tert.-butanol, 60 ml of i-butene and 3 ml of concentrated sulfuric acid are mixed at −15° C. and stirred vigorously in an autoclave at room temperature for 24 hours.

The reaction mixture is again cooled to −15° C. and stirred into excess sodium bicarbonate solution, which is then extracted with methylene chloride, and the extracts are finally evaporated in vacuo.
Yield: 20.4 g (67% of theory). The product is recrystallized from hexane.

$^1$H NMR (CDCl$_3$): δ=1.4 (s); 2.6 (m); 3.0 (t); 7.4 (m); 7.95 (m). MS: m/z=305 (M$^+$H)

3-(4-Chlorsulfonylphenyl)-propionic acid was prepared in a known manner from 2-phenylpropionic acid and chlorosulfonic acid.

4-(Morpholino-N-2-ethoxy)aniline (7-a2)

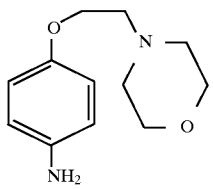

(7-a2)

25 g (0.1 mole) of 4-(morpholino-N-2-ethoxy) nitrobenzene are refluxed with 75 g of granulated zinc in 400 ml of 50% concentrated hydrochloric acid for 4 hours. The mixture is cooled and then poured into 400 ml of 33% strength hydrochloric acid, the mixture is extracted with i-propyl ether, and the organic phase is dried and then evaporated. 20 g (90% of theory) of desired product are obtained.

$^1$H NMR (CDCl$_3$): δ=2.5 (t); 2.7 (t); 3.5 (broad); 3.7 (t); 4.0 (t); 6.6 (m) MS: m/z=222 (M$^+$)

The same product is obtained by hydrogenation of the nitro compound on palladium/animal charcoal in methanol. The nitro compound was prepared by the method of Bull. Soc. chim. France 1955, 1353–62.

N-[4-(Morpholino-N-2-ethoxy)phenyl]-N-[4-(2-t-butoxycarbonylethyl)phenylsulfonamide] (7-a3)

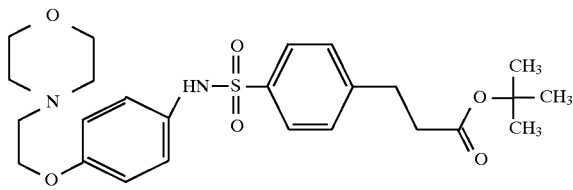

(7-a3)

The solution of 9.3 g (30 mmol) of t-butyl 4-chlorosulfonylphenylpropionate, 6.9 g of 4-(morpholino-N-2-ethoxy)aniline and 0.3 g of dimethylaminopyridine in 150 ml of methylene chloride, which is clear after standing at room temperature for 10 hours, is washed with saturated sodium bicarbonate solution, concentrated to ⅓ and chromatographed on a kieselguhr column with a mixture of 90% methylene chloride and 10% methanol. The main fraction of the eluate is evaporated.

Yield: 9 g (61.2% of theory) $^1$H NMR (CDCl$_3$): δ=1.35 (s); 2.5 (m); 2.7–3.0 (m); 3.7 (m); 4.0 (t); 6.7–7.0 (m); 7.2–7.7 (m) MS: m/z=491 (M$^+$H).

N-[4-(Morpholino-N-2-ethoxy)phenyl]-N-[4-(2-t-butoxycarbonylethyl)phenylsulfonyl]-9-acridinecarboxamide (7-a4)

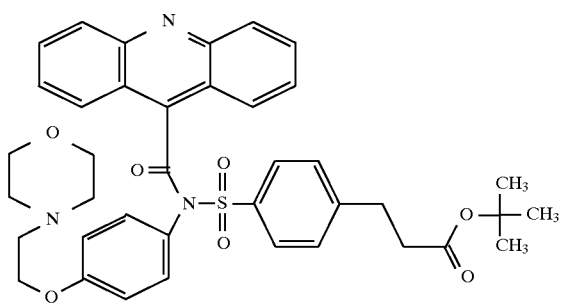

(7-a4)

50 ml of 33% strength sodium hydroxide solution, 30 mg of dimethylaminopyridine, 1.2 g of tetrabutylammonium chloride and 1.55 g (5.6 mmol) of 9-acridinecarbonyl chloride hydrochloride are successively added to a vigorously stirred solution of 2.0 g (4.1 mmol) of N-[4-morpholino-N-2-ethoxy)phenyl]-N-[4-(2-t-butoxycarbonylethyl)-phenylsulfonamide] in 50 mL of methylene chloride. After 6 hours, the organic phase is separated off, washed with water, dried over sodium sulfate and evaporated.

Yield: 2.8 g (98% of theory) $^1$H NMR (CDCl$_3$): δ=1.4 (s); 2.3–2.5 (m); 2.5–2.8 (m); 3.0–3.3 (t); 3.6–3.9 (m); 6.3 (d); 6.9 (d); 7.4–8.3 (m). MS: m/z=695 (M$^+$)

N-[4-(Morpholino-N-2-ethoxy)phenyl]-N-[4-(2-carboxyethyl)-phenylsulfonyl]-9-acridinecarboxamide (7-a5)

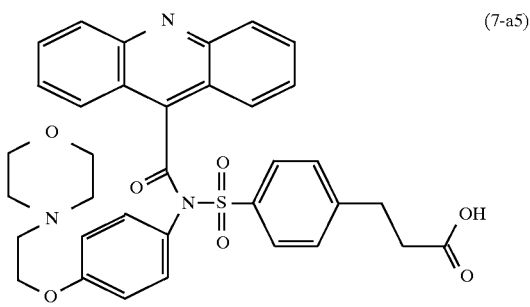

(7-a5)

0.7 g (1 mmol) of N-[4-(morpholino-2-ethoxy)phenyl]-N-[4-(2-t-butoxycarbonylethyl)phenylsulfonyl]-9-acridinecarboxamide is dissolved in 5 ml of trifluoroacetic acid and Left to stand at room temperature overnight. The mixture is evaporated under waterpump vacuum, the residue is dissolved in water, and the filtered solution is neutralized to pH 4 with sodium acetate. The resulting product is extracted with methylene chloride, dried over sodium sulfate and evaporated.

Yield: 0.6 g (94% of theory) $^1$H NMR (DMSO): δ=2.6–3.0 (m); 3.0–3.3 (m); 3.6–4.0 (m); 4.0–4.4 (m); 5.8–6.6 (m); 6.8–7.0 (m); 7.3–8.4 (m). MS: m/z 639 (M$^+$)

N-[4-(Morpholino-N-2-ethoxy)phenyl]-N-[4-(2-succinimidyloxycarbonylethyl )phenylsulfonyl ]-9-acridinecarboxamide (7-a6)

Yield: 95% of theory $^1$H NMR (CDCl$_3$): δ=2.3–2.7 (m); 2.8 (s); 2.9–3.4 (m); 3.5–3.9 (m); 3.9–4.3 (m); 6.2–7.0 (m); 7.3–8.3 (m). MS: 736 (M$^+$)

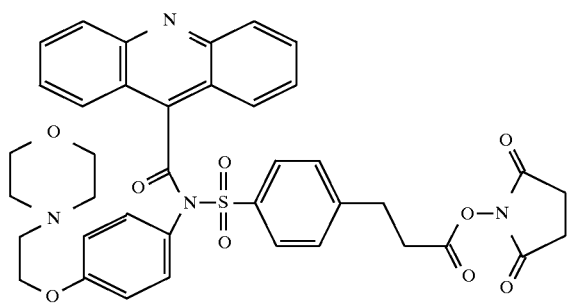

(7-a6)

N-[4-(N-Methylmorpholino-N-2-ethoxy)phenyl]-N-[4-(2-succinimidyloxycarbonylethyl)phenylsulfonyl]-10-methylacridine-9-carboxamide diium difluorosulfonate (7-a7)

Yield: 84% of theory The compound gives a clear yellow-colored solution in water. $^1$H NMR (DMSO): δ=2.85 (s); 3.1 (s); 3.2–4.4 (m); 4.75 (s); 6.4–8.3 (m)

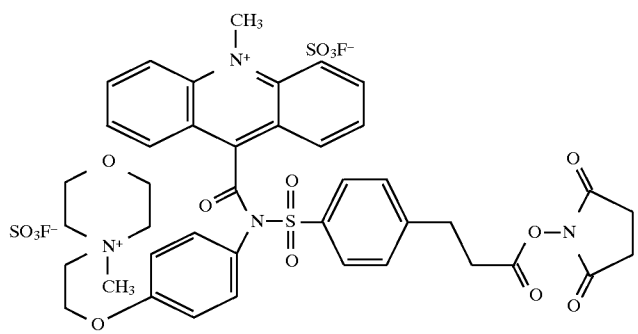

(7-a7)

EXAMPLE 8

Preparation of tracer for the TSH chemiluminescence immunoassay

91 μl of antibodies (100 pg), 20 μl of the acridinium derivative prepared as in EXAMPLE 1 (compound (6)) (1 mg/ml in acetonitrile) and 600 μl of conjugation buffer (0.01M phosphate, pH 8.0) are incubated for 15 minutes. Then 200 μl of Lysine (10 mg/mL in conjugation buffer) are added, and the mixture is incubated for a further 15 minutes. This mixture is applied to a PD 10 column (Sephadex® G 25 medium, (crosslinked dextran gel in the form of beads, manufactured by Pharmacia, Sweden)) and eluted with 0.1M phosphate, pH 6.3, as mobile phase. 10 drops/fraction are collected. The individual fractions are diluted suitably and then tested for their chemiluminescence activity (350 μl of oxidizing agent: 0.1% H$_2$O$_2$ in 0.1N NaOH). The tracer fractions (1st activity peak) are pooled and stored at 4° C. The tracer which is ready for use for the h-TSH chemiluminescence immunoassay is prepared by suitable dilution with a phosphate buffer (0.1M phosphate, pH 6.3, 1% Tween® 20 (polyethylene sorbitan monolaurate manufactured by, for example, ICI American Inc., USA), 0.1% bovine serum albumin, 0.1M NaCl, 0.01% NaN$_3$).

EXAMPLE 9

Procedure for the h-TSH chemiluminescence immunoassay

50 μl of standard/sample and 200 μl of tracer were shaken at room temperature for 2 hours in tubes coated with monoclonal anti-TSH antibodies. Washing 3× with 1 ml of buffer and distilled water is then carried out. The light emission is effected by addition of, in each case, 300 μl of activating reagent (pH 1 buffer, 0.5% H$_2$O$_2$) and 300 μl of initiator reagent (0.2N NaOH) via 2 dispensers in the luminometer into the tubes. The measuring time is 1 sec.

FIG. 3 shows the typical shape of a standard plot of an immunochemiluminometric assay (ICMA) for human thyroid-stimulating hormone (h-TSH).

We claim:

1. A luminescence immunoassay, which comprises the step of measuring the presence of an antigenic substance in a liquid sample by a competitive or sandwich assay method using at least one immunologically active component immobilized on a solid phase and a stable immunologically active tracer conjugate formed of a substance of biological interest bonded directly or indirectly to an acridinium derivative of formula I

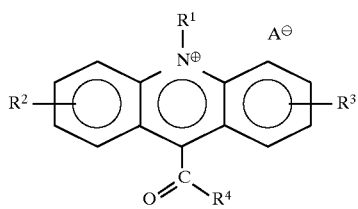

in which
R¹ is hydrogen, an alkyl radical having 1 to 10 carbon atoms, an alkenyl or alkynyl radical having 2 to 10 carbon atoms, or a benzyl or aryl group, R² and R³ are hydrogen, a halogen atom, an alkyl group having 1 to 4 carbon atoms, a carboxyl, alkoxy, cyano, nitro group, or a substituted or unsubstituted amino group, R⁴ represents a radical having formula II as follows:

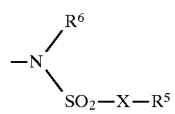

in which
R⁵ is a radical selected from the group consisting of:

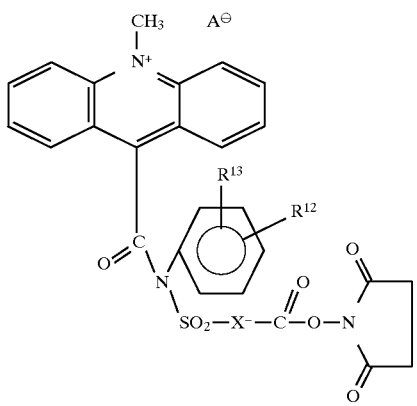

X denotes an an amino carboxylic acid group, or a phenylene group, wherein the phenylene group is bonded to the sulfur atom directly or via an alkylene or oxyalkylene group or is bonded to the R⁵ radical via an alkylene or oxyalkylene group, the phenylene group may be substituted one or more times by alkyl, alkenyl, hydroxyl, amino, alkoxy, or aryloxy groups, R⁶ is a phenyl group substituted by an (—O—CH₂—CH₂)$_n$—OR group, where n is 0–8 and R is an N,N-dimethyl-aminoethyl group, or a morpholinoethoxy group that may be substituted at its nitrogen atom by an alkyl group, or R₆ may be an ethylenedioxyphenyl group and A ⊖ is an anion that does not adversely interfere with chemiluminescence.

2. The luminescence immunoassay of claim 1, comprising:
incubating in the liquid sample an immobilized antibody, which binds specifically with an antigenic substance in said liquid sample, together with said tracer conjugate, in which said substance of biological interest is said antigen;

separating the liquid sample and any unbound tracer conjugate;

contacting the bound conjugate successively or simultaneously with one or more reagents to bring about light emission; and measuring the intensity of the light emission to determine the amount of antigenic substance present in the liquid sample.

3. The luminescence immunoassay of claim 2, wherein the liquid sample is separated from the immobilized antibody before the addition of the active tracer conjugate.

4. The luminescence immunoassay of claim 1, comprising:
incubating in the liquid sample an immobilized antibody, which reacts specifically with an antigenic substance in the liquid sample, together with said tracer conjugate, in which said substance of biological interest is a second specifically reacting antibody;

separating the sample and any unbound tracer conjugate;

contacting the bound tracer conjugate successively or simultaneously with one or more reagents to bring about light emission; and measuring the intensity of the light emission to determine the amount of antigenic substance present in the liquid sample.

5. The luminescence immunoassay of claim 4, wherein the liquid sample is separated from the immobilized antibody before the addition of the active tracer conjugate.

6. The luminescence immunoassay of claim 1, comprising:
incubating in the liquid sample an immobilized antigen, which reacts specifically with an antibody, together with a solution of said tracer conjugate, in which said substance of biological interest is said antibody;

separating the sample and any unbound tracer conjugate;

contacting the bound tracer conjugate successively or simultaneously with one or more reagents to bring about light emission; and measuring the intensity of the light emission to determine the amount of antigenic substance present in the liquid sample.

7. The luminescence immunoassay of claim 1, comprising:
incubating an immobilized antigen, which reacts specifically with an antibody, with a solution of said tracer conjugate, in which said substance of biological interest is said antibody;

separating any unreacted conjugate;

adding the liquid sample containing the antigenic substance;

separating off the liquid sample;

contacting reacted tracer conjugate successively or simultaneously with one or more reagents to bring about light emission; and measuring the intensity of the light emission to determine the amount of antigenic substance present.

8. The luminescence immunoassay of claim 1, comprising:
incubating an immobilized antigen, which reacts specifically with an antibody, with a solution of said tracer conjugate, in which said substance of biological interest is said antibody;

adding the liquid sample containing the antigenic substance;

separating the sample and any unbound tracer conjugate;

contacting bound tracer conjugate successively or simultaneously with one or more reagents to bring about light emission; and measuring the intensity of the light emission to determine the amount of antigenic substance present in the liquid sample.

9. The luminescence immunoassay of claim 1, wherein X is a p-ethylenephenyl group and $R^5$ is an N-succinimidyloxycarbonyl radical.

10. The luminescence immunoassay of claim 9, wherein $R^1$ is methyl and $R^2$ and $R^3$ are each hydrogen.

11. The luminescence immunoassay of claim 10, wherein $R^6$ is 4-methyloxyphenyl.

12. The luminescence immunoassay of claim 10, wherein $R^6$ is 2,4-dimethoxyphenyl.

13. The luminescence immunoassay of claim 10, wherein $R^6$ is 4-(N-methylmorpholino-N-2-ethoxy)phenyl.

14. The luminescence immunoassay of claim 1, wherein X is a p-ethylenephenyl group, $R^1$ is methyl, $R^2$ and $R^3$ are each hydrogen, $R^5$ is a butoxycarbonyl group, and $R^6$ is 4-(morpholino-N-2-ethoxy)phenyl.

15. A luminescence immunoassay, which comprises the step of measuring the presence of an antigenic substance in a liquid sample by a competitive or sandwich assay method using at least one immunologically active component immobilized on a solid phase and a stable immunologically active tracer conjugate formed of a substance of biological interest bonded directly or indirectly to an acridinium derivative of the formula:

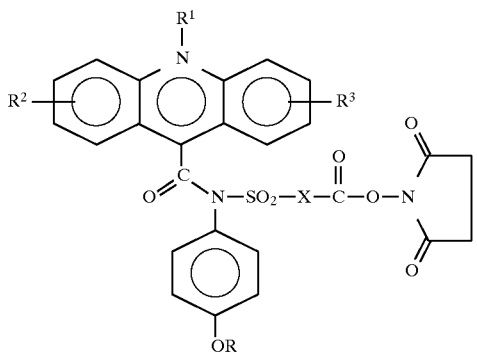

in which $R^1$ is hydrogen, an alkyl radical having 1 to 10 carbon atoms, an alkenyl or alkynyl radical having 2 to 10 carbon atoms, or a benzyl or aryl group, $R^2$ and $R^3$ are hydrogen, an alkyl group having 1 to 4 carbon atoms, a carboxyl, alkoxy, cyano, nitro group, or a substituted or unsubstituted amino group, X represents

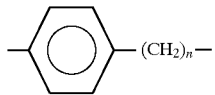

and n is 2 or 4

R is an alkyl group having 1–4 carbon atoms, and

A (-) is an anion that does not adversely interfere with chemiluminescence.

* * * * *

UNITED STATES PATENT AND TRADEMARK OFFICE
CERTIFICATE OF CORRECTION

PATENT NO. : 5,879,953  
DATED : March 9, 1999  
INVENTOR(S) : Tonio Kinkel et al.

Page 1 of 1

It is certified that error appears in the above-identified patent and that said Letters Patent is hereby corrected as shown below:

Claim 1, column 29,  
Lines 30-40, delete Formula "(VI)" in its entirety and replace with

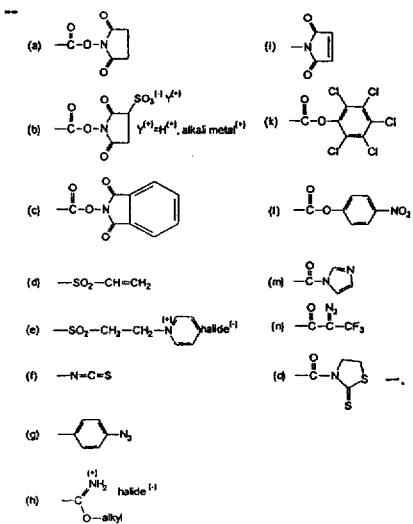

Line 67, change "said antigen" to -- antigenic substance --.

Signed and Sealed this

Eighteenth Day of September, 2001

Attest:

NICHOLAS P. GODICI  
Attesting Officer  
Acting Director of the United States Patent and Trademark Office